United States Patent [19]
Johnson et al.

[11] Patent Number: 5,304,147
[45] Date of Patent: Apr. 19, 1994

[54] INJECTION SYRINGE

[75] Inventors: Thomas R. Johnson, Milford; Andrew L. Cote, Sr., Peterborough, both of N.H.

[73] Assignee: Johnson Medical Development Corp., Milford, N.H.

[21] Appl. No.: 972,612

[22] Filed: Nov. 6, 1992

Related U.S. Application Data

[63] Continuation-in-part of Ser. No. 750,416, Aug. 27, 1991, abandoned.

[51] Int. Cl.$^5$ .................. A61M 5/178; A61M 5/315
[52] U.S. Cl. ................... 604/183; 604/223; 604/228; 604/236; 604/247; 222/383
[58] Field of Search ............ 604/48, 51, 60-64, 604/70, 71, 121, 183, 186, 222, 223, 227, 228, 233, 236, 237, 247, 218; 222/324, 383, 509

[56] References Cited

U.S. PATENT DOCUMENTS

| | | | |
|---|---|---|---|
| 1,982,993 | 6/1934 | Kauzal | 128/223 |
| 1,995,971 | 3/1935 | Dowling | 604/183 |
| 2,709,025 | 3/1953 | Scott | 222/341 |
| 3,384,081 | 5/1968 | Castiglione | 604/183 |
| 3,949,073 | 4/1976 | Daniels et al. | 128/DIG. 8 |
| 4,020,838 | 5/1977 | Phillips et al. | 604/186 |
| 4,204,539 | 5/1980 | Van Brugge | 604/183 |
| 4,342,310 | 8/1982 | Lindmayer et al. | 604/70 |
| 4,639,019 | 1/1987 | Mittleman | 604/283 |
| 4,664,298 | 5/1987 | Shew | 222/287 |
| 4,718,894 | 1/1988 | Lazorthes | 604/93 |
| 4,837,285 | 1/1989 | Berg et al. | 128/DIG. 8 |
| 4,838,866 | 1/1989 | Marshall, Sr. | 604/236 |

Primary Examiner—C. Fred Rosenbaum
Assistant Examiner—Mark Bockelman
Attorney, Agent, or Firm—Hayes, Soloway, Hennessey, Grossman & Hage

[57] ABSTRACT

An injection syringe useful in the medical arts for injecting high viscosity fluids or pastes, particularly in endoscopic applications. The syringe includes a force multiplying mechanism to infuse viscous medicaments such as collagen or polytetrafluoroethylene paste, with a controlled metering action. The force multiplying mechanism is provided by the combination of lower piston cylinder chamber that intersects with an upper cylinder chamber, wherein the piston is connected to a piston advancing means on a lever pivot arm.

45 Claims, 2 Drawing Sheets

INJECTION SYRINGE

CROSS REFERENCE TO RELATED APPLICATION

This application is a continuation-in-part of U.S. application Ser. No. 07/750,416, filed Aug. 27, 1991 now abandoned.

FIELD OF THE INVENTION

This invention relates to an apparatus and method for the injection of high viscosity liquids or pastes. The invention has particular utility as an injection syringe useful for injecting such liquids or pastes in surgical procedures, especially in endoscopic procedures, and will be described in connection with such utility, although other utilities are contemplated.

BACKGROUND OF THE INVENTION

The present invention relates to an injection syringe, particularly for medical purposes, for injecting high viscosity liquids or pastes. In particular, the present invention relates to an injection syringe suitable for endoscopic correction of vesicoureteral reflux.

Vesicoureteral reflux amounts to a reflux of urine from the bladder into the ureter and predisposes an individual to damage of the upper urinary tract by bacterial infection and by increased hydrostatic pressure. Vesicoureteral reflux is most often due to a congenital malimplantation of the ureter into the bladder; incomplete development of the intramural ureteral tunnel causes a failure of the valvelike action at the ureterovesical junction and permits the reflux of bladder urine into the ureter and renal pelvis, particularly under the increased intravesical pressures of voiding. Other causes of vesicoureteral reflux include bladder outlet obstruction with increased intravesical pressures, lower urinary tract infection with edema and distortion of ureteral orifice, neurogenic dysfunction of the detrusor and vesical neck mechanism, and iatrogenic reflux secondary to surgical or instrumental manipulation of the ureteral orifice. See, "The Merck Manual of Diagnosis and Therapy", Published by Merck Sharp & Dohme Research Laboratories (1977).

Treatment of reflux is either medical or surgical. Medical management is based on the observation that vesicoureteric reflux tends naturally to improve with time. Surgical treatment generally entails opening the bladder and performing a variety of procedures on the ureter. An alternative method of treatment considers intravesical injection of Teflon paste into the space behind the ureter. See, e.g. P. Puri and B. O'Donnell, The British Medical Journal, Vol. 289, July 1984; A. Farkas et al, The Journal of Urology, Vol. 144, August 1990.

Accordingly, injecting syringes have been developed to respond to the need for a delivery system which can readily inject the high viscosity substances described above. The known injecting syringes of this type are constructed inter alia with long injection cannula, which are slightly elastic and can be introduced into a corresponding channel of an endoscope. One example of such a device is described in U.S. Pat. No. 4,276,878. See also U.S. Pat. Nos. 4,432,753; 4,020,838; 3,682,175; 3,353,537; 3,104,448; 2,821,195 and 1,982,993.

However, problems with the above designs include the relatively large diameter of the pistons required to advance the high viscosity material through a long and relatively small diameter opening. Furthermore, earlier devices have not provided a means to continuously deliver high viscosity liquids or pastes without the need to continuously refill the particular piston chamber. Finally, existing designs cannot be tailored to a variety of viscosities and pressures.

One extremely early attempt to develop a pumping mechanism that may have been suitable for adaption in an injection syringe of the type contemplated herein, was described in U.S. Pat. No. 731,033 (1903). This particular pumping mechanism included a tubular fluid-circulating chamber formed at one end with an inlet neck, and containing at its opposite end an outlet neck, wherein the inlet neck was fitted with an inwardly opening check valve permitting fluid to enter the circulating chamber and close in a direction to prevent backflow of fluid. The outlet neck was described as having an outwardly-opening check valve, to permit the discharge of fluid from the chamber under the input of a pumping action.

This particular design, however, made no mention of the fact (as described herein) that a ball-bearing type check valve, of varying durometer, in combination with adjustment of the inlet and outlet port size, together provides a pumping mechanism that "self-throttles", i.e. one in which the pumping action is restricted or rendered impossible over a certain desired and targeted range of internal delivery pressure.

Another early attempt to develop an injection syringe was reported in Australian Patent Specification 126,075 (1945). This particular design employed the use of a vertically mounted diaphragm which effected the actual displacement of liquid from a single an upper horizontal hollow chamber. However, it was specifically suggested that more complete piston designs would leak or stick and be more difficult to clean or provide a moving mechanism.

In U.S. Pat. No. 4,664,298 there is described a hand lever operated grease gun that has both high pressure and high volume modes afforded by changing the mechanical advantage of a lever acting on a dispensing piston. Although this particular reference also disclosed check valves in combination with a single piston for fluid delivery, it also failed to appreciate how important the selection of materials, and the size of the inlet and outlet ports were to the control of internal delivery pressure. Furthermore, unlike the present invention which uses single-arm control, this reference describes a dual-arm level action for fluid delivery.

Other related art, e.g. French Pat. 275017 and U.S. Pat. Nos. 2,709,025 and 1,982,993 describe fluid delivery systems, but none of these references solve the problem of providing a fluid delivery system for high viscosity pastes in the novel manner that is herein described.

Accordingly, it is an object of this invention to obviate these disadvantages and to provide an injection syringe that easily delivers a much higher pressure to fluid or paste, so that the fluid or paste is advanced with maximum reliability and avoids sticking in a piston chamber or cannula of the device.

It is a further object of this invention to provide an injection syringe wherein a high viscosity paste of fluid is continuously fed into a piston chamber so that a continuous source of fluid or paste can be delivered to a desired location within a body cavity.

It is also an object of this invention to accomplish the above through the convenience of operation of a pistollike handle/lever combination injector which can be easily handled and which is arranged to develop a high pressure force in a cylinder chamber.

It is still further object of this invention to develop a high pressure force in a cylinder chamber via a lever pivot arm which contains a piston advancing means and which is connected thereby to a piston in a lower piston cylinder chamber which intersects and connects to the upper cylinder chamber of the syringe and thereby readily promotes a steady flow of high viscosity material.

It is also an object of this invention to develop a method for delivering high viscosity fluids, pastes or medicaments to a particular body cavity preferably in conjunction with the endoscopic injection and correction of primary vesicoureteric reflux and urinary incontinence.

Finally, is an object of this invention to provide an injection syringe wherein management of the internal delivery pressure is achieved by adjustment of inlet and outlet port size and the durometer of the inlet and outlet ball-bearing check valve.

BRIEF SUMMARY OF THE INVENTION

The present invention provides an apparatus and a method for the injection of high viscosity pastes or liquids. The apparatus comprises a frame, a pair of handles mounted to said frame, at least one of which is a level pivotally mounted to said frame and incorporating a piston advancing means, an upper and lower cylinder chamber, said upper chamber containing an inlet and outlet port, a one way ball-bearing inlet valve seated at the inlet port, a one way ball-bearing outlet valve seated at the outlet port, said lower chamber containing a piston connected to the piston advancing means on the lever pivot arm, wherein the durometer of inlet and outlet ball-bearing and the size of the inlet and outlet ports are adjusted to regulate the maximum internal delivery pressure in the upper cylinder chamber. In addition, the delivery pressure can be varied according to the size of the cylinder chamber, location of the pivot point on the lever arm, the size of the lever arm, and the geometry of the track which advances the piston.

BRIEF DESCRIPTION OF THE DRAWINGS

The invention is described in greater detail hereinafter relative to non-limitating embodiments and with reference to the drawings, in which.

DETAILED DESCRIPTION OF THE PREFERRED EMBODIMENTS

Figure 1:
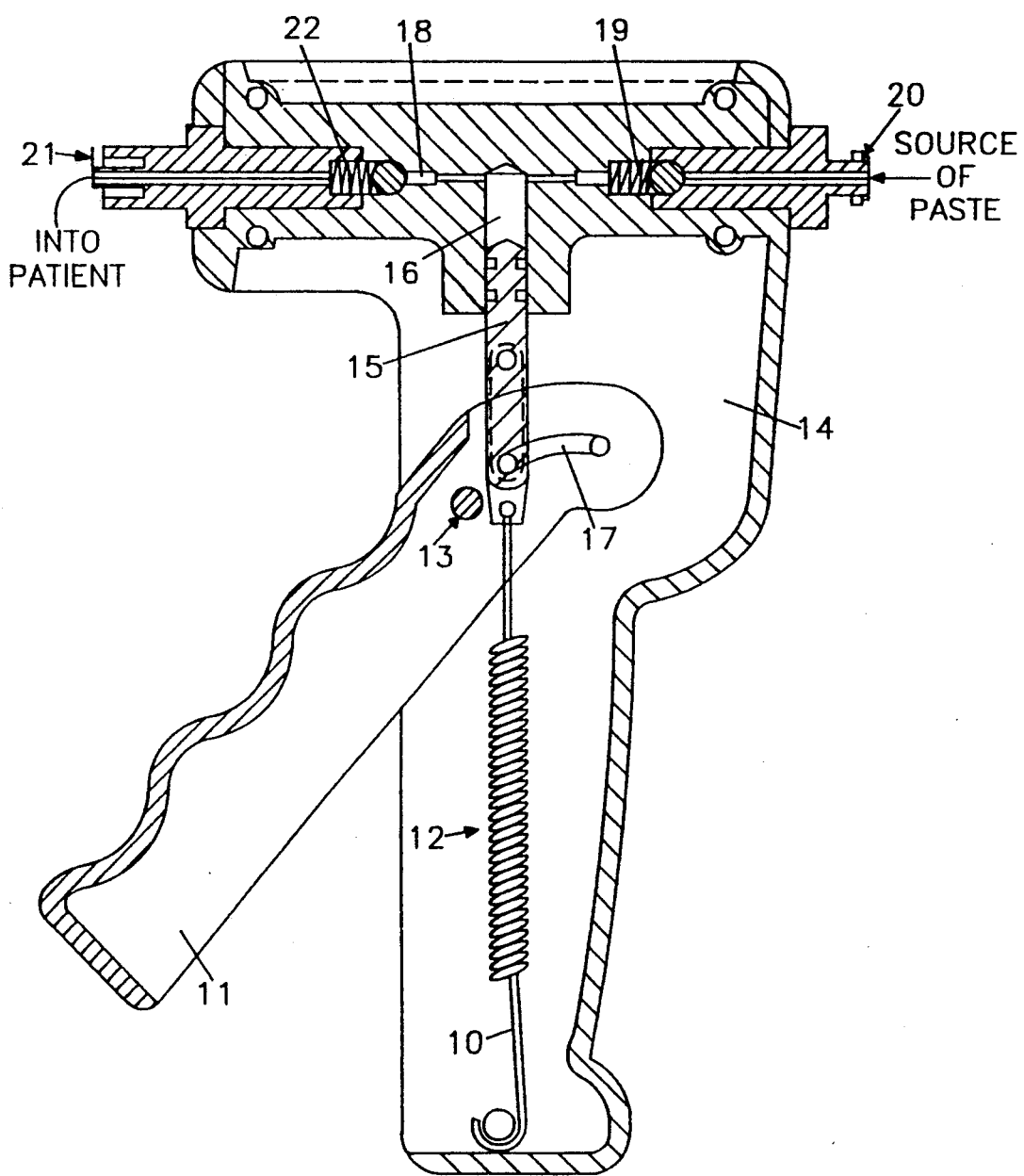
FIG. 1 shows an embodiment of the injection syringe according to the invention in a cross-sectional view.

FIG. 1 shows the two gripping handles, 10 and 11, between which are arraigned a spring 12, which serves to force gripping handle 11 into the position as shown. At least one of the gripping handles 11 is relatively pivotable about point 13. That portion of handle 14 above point 13 is sometimes referred to as a "frame". The handles, 10 and 11, are sometimes collectively referred to as "grip means". The gripping handle system is conventionally used for advancing the piston 15 which is slidably mounted and can be sealingly engaged in the lower cylinder piston chamber 16 through an elastomeric O-ring seal. Within the gripping handle pivotally mounted at point 13, also known as the pivotally mounted lever, can be seen a piston advancing means 17 which serves to reciprocally drive the piston 15 in the piston chamber when the gripping handles are brought together and apart in a pumping type action. The piston advancing means can be of any type of geometry designed to optimize the force brought to the piston during the pumping action of the handles. In a preferred embodiment, the piston advancing means comprises a semi-circular cam track, which allows for a smooth reciprocal motion of the piston in the piston chamber. An upper elongated cylinder chamber 18 contains at one end a one-way ball-bearing inlet check valve 19 whereby a feed of high viscosity paste or fluid to be discharged can be attached and drawn into the cylinder through the inlet check valve which then restricts material from moving back into the source of fluid or paste. The supply of feed 24 can be connected at 20 through a luer type connection. On the other end of the cylinder chamber 21, an injection cannula 23 can be mounted and an outlet one-way ball-bearing bearing check valve 22 restricts material from moving back into the syringe. It can be seen that the elongated cylinder 18 can project beyond the frame 14 and the length of the cylinder can be a substantial multiple of its diameter. The injection syringe as described can be manufactured from either a plastic or stainless steel material, or a combination of such materials, depending upon the particular application and viscosity of fluids and pastes to be delivered. Furthermore, depending on the manufacturing materials so selected, the instant device can be made reusable or disposable.

It has now been found that the durometer of the inlet and outlet ball-bearing, and the size of the inlet and outlet ports, can both be adjusted to regulate the maximum internal delivery pressure in the upper cylinder chamber. This is so because the hardness of the ball-bearing controls the point at which the ball bearing is compressed by the upward action of the piston to become lodged in either of the two ports. The higher the hardness of the ball-bearing, the higher the internal delivery pressure achieved, and vice versa.

Alternatively, if the size of the ports is changed, for example, to a larger size opening, a lower pressure will suffice to lodge the ball bearing in the port preventing any further delivery of paste or liquid. In this manner it is now uniquely possible (by the emperical selection of durometer ball-bearing and/or port-size) to provide an injection syringe that "self and/or throttles", i.e. the maximum delivery pressure being regulated to a targeted level.

Any suitable elastomeric type material can be used for the ball bearing, provided it does not chemically interact with the paste or fluid to be delivered. In a preferred embodiment, fluoropolymer elastomers are employed, and a particularly preferred fluoroelastomer is a material known as Viton, available from the DuPont Chemical Company. In accordance with the present invention, a Viton material with a 70D Shore Hardness, in combination with a port size of about 0.104 inch, maintained a limit on the internal delivery pressure of about 850 psi.

Figure 2:
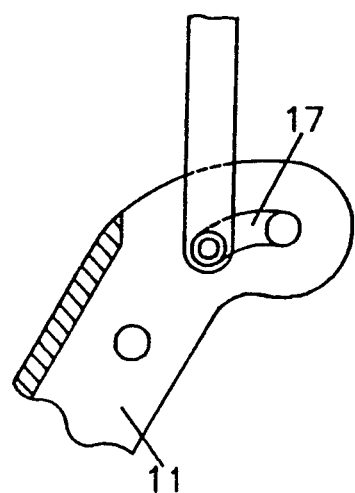
FIG. 2 shows a cross-sectional view of the piston advancing means in the pivot lever handle.

FIG. 2 provides a more expanded view of the piston advancing means 17 within the pivotally mounted lever 11. As can now be more fully appreciated, when the pivotally mounted lever is brought together with the gripping handle 10, the piston advancing means drives the piston upwards and into the lower piston cylinder chamber 16. At that point, the compression developed in both the lower and upper cylinder chambers causes the inlet one-way valve at 19 to close, the outlet one-way valve at 22 to open, wherein the high viscosity paste or fluid is delivered to the end of the cylinder chamber at 21. Accordingly, when the pivotally mounted lever 11 is moved apart from the gripping handle 10, a vacuum is developed within the cylinder chambers which causes the outlet one-way valve 21 to close, the inlet one-way valve 19 to open, and a flow of high viscosity paste or fluid into the device. FIG. 2 also illustrates that the position of the pivot point 13 can be altered to either increase or decrease the amount of force delivered to the piston through the piston advancing means. Accordingly, it can be appreciated that a variation in the location of the pivot point 13, along with the length of the pivotally mounted lever 11 optionally provides an adjustment to the quantity of force required to deliver pastes or liquids of different viscosities. Finally, it can be appreciated that the geometry of the cam face can be adjusted so that the rise of the piston in the final stages of compression exerts a large force to the piston.

Figure 3:
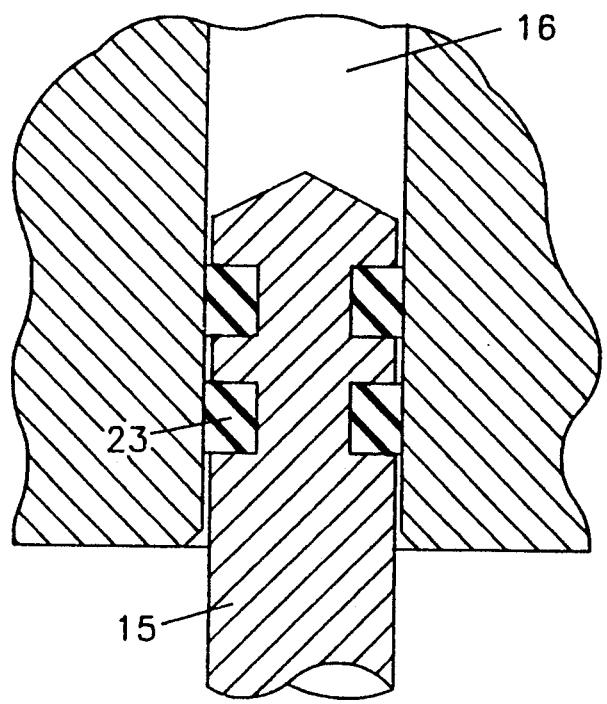
FIG. 3 shows a cross-sectional view of the piston including the placement of an elastomeric O-ring seal.

As shown in FIG. 3, piston 15 optionally contains an elastomeric O-ring type seal which serves to sealingly engage the piston with the lower piston cylinder chamber 16. It has been found that such O-rings can be manufactured from any type of elastomeric or rubbery material. For example, it has been found that silicon type elastomers are especially suited for this application. In general, those elastomers that are selected must physically withstand the pressures and vacuums required for delivery of a high high viscosity fluids or pastes, while at the same time remaining chemically inert so as not to significantly contaminate the fluid or paste that is finally delivered to a targeted location.

As noted supra, the injection syringe of the present invention has particular utility in the medical field, e.g. for introducing high viscosity fluids or pastes into a patient's body. The syringe is charged by drawing together the handle/lever combination against the retractive force of the tension spring followed by release wherein the lever returns to its original position and wherein the pumping action develops a repeated vacuum within the cylinders afforded by the piston downstroke. The vacuum within the cylinders operates to cause the one-way outlet valve to seal, the one-way inlet valve to open, which then charges and fills the syringe with a steady feed of material. Continued pumping action advances the fluid or paste wherein the upstroke of the piston provides compression to the cylinder chambers, at which point the one-way inlet valve seals and the outlet valve opens and the fluid or paste is delivered to a body cavity and further restricted from moving back into the syringe. To this end the high viscosity fluid or paste can be introduced to the instrument channel of a medical endoscope providing a method of treatment of vesicoureteral reflux and urinary incontinence, as well as treatment of other types of medical problems that require injection of a viscous medicament. The high viscosity fluids or pastes include materials such as collagen and polytetrafluoroethylene particles suspended in glycerine and polysorbate.

It has also been found that the injection syringe of the present invention has particular utility in connection with thrombolysis catheters which are used to treat emboli in the venous system. Currently, thrombolysis agents are used in conjunction with catheters of a small diameter, typically a 3 F injectable guide wire with a 0.025 inside diameter along with urokinase and TPA (tissue plasminogen activator), Prourokinese APSAC (antistreplase), Eminase and similar agents. The infusion of these agents has been hampered by current delivery systems which typically have been 1 or 2 cc syringes requiring frequent refilling and limited pressures to propel these agents through the small diameters and long lengths of the catheters used in these procedures. The new device addresses these problems by allowing a self-feeding system and the high pressure required for an effective procedure.

As described above, the current invention is useful in the medical arts for injecting or delivering high viscosity pastes, fluids or medicaments to a particular region of a body where a large force is required to advance such medications because of the elevated viscosity and/or the small diameter and long length of the cannula or catheter through which the medication is injected. The device incorporates a piston actuated by a lever which utilizes the mechanical advantage of a pivot arm and a piston advancing means which advances the piston in a lower cylinder chamber. The amount of pressure generated by the combination of the diameter of the cylinders, geometry of the piston advancing means, pivot point and lever arm, can be collectively tailored to a variety of medicament viscosities.

Those skilled in the art will recognize, or be able to ascertain, by no more than routine experimentation, many equivalents of the specific embodiments of the invention described herein. Moreover, the syringe may advantageously be used for injecting other liquids or pastes in non-medical applications, e.g. for delivering high viscosity glues or lubricants. Such equivalence are intended to be encompassed by the following claims.

What is claimed is:

1. An injection syringe for the injection of high viscosity paste or liquid, comprising a frame, a pair of handles mounted to said frame, at least one of which handles is a lever pivotally mounted to said frame incorporating a piston advancing means, an upper and lower cylinder chamber providing fluid connection therebetween, said upper chamber containing an inlet and outlet port, a one way ball-bearing inlet valve seated at the inlet port, a one way ball-bearing outlet valve seated at the outlet port, said lower cylinder chamber containing a piston having means connecting the piston to the piston advancing means on the lever pivot arm, wherein the inlet and outlet ball-bearings have durometers which are chosen to regulate the maximum internal delivery pressure in said upper cylinder chamber, wherein the piston advancing means comprises a semi-circular cam track slidably engaging the piston connecting means for upwardly advancing said piston into said lower piston cylinder chamber as the piston connecting means slides along said cam track so that substantially all of the liquid or paste in the cylinders is forced through the one-way valve in the outlet cylinder chamber.

2. The injection syringe of claim 1 wherein the upper cylinder chamber projects beyond said frame.

3. The injection syringe of claim 1 which further includes an end space on the outlet side of the upper cylinder chamber to which an injection cannula can be mounted.

4. The injection syringe of claim 1 in which the inside diameter of the injection cannula at its end farthest from the end space on the outlet side of the upper cylinder chamber is smaller than the inside diameter of the cylinder.

5. The injection syringe of claim 4 in which the injection cannula is a needle.

6. The injection syringe of claim 4 in which the injection cannula is a catheter.

7. The injection syringe of claim 1 wherein a reservoir of high viscosity fluid or paste is attached by a connecting means to the inlet side of the upper cylinder chamber.

8. The injection syringe of claim 7 wherein the reservoir connecting means is a luer type connection.

9. The injection syringe of claim 1 wherein the length of the upper cylinder is a substantial multiple of its diameter.

10. The injection syringe of claim 1 in which the piston sealingly engages the corresponding piston cylinder wall through an elastomeric O-ring seal.

11. The injection syringe of claim 1 wherein an extension spring is attached to the pivotally mounted handle so as to provide a retractive force to said handle.

12. The injection syringe of claim 1 wherein the syringe is manufactured from a plastic material.

13. The injection syringe of claim 1 wherein the syringe is manufactured from stainless steel.

14. The injection syringe of claim 1 wherein the one-way inlet and outlet ball-bearing valves are made from a fluoroelastomer material.

15. A method for introducing high viscosity medicaments into a patient comprising:
supplying the injection syringe of claim 1; and
charging the syringe by compressing and releasing the handle/lever combination wherein the pumping action provides a vacuum, within the cylinders upon the downstroke of the piston and wherein the outlet ball-bearing valve seals and the inlet ball-valve bearing valve opens thereby charging the syringe; and
advancing the medicament through the outlet check valve by a continued pumping action wherein the upstroke of the piston provides compression to the chambers and the inlet check valve seals and the outlet valve opens and the medicament is introduced into a body and restricted from moving back into the syringe.

16. The method of claim 15 wherein the high viscosity medicament is introduced into a medical endoscope.

17. The method of claim 15 wherein the high viscosity medicament is a suspension of polytetrafluoroethylene particles in glycerine and polysorbate.

18. The method of claim 15 wherein the high viscosity medicament is collagen.

19. The method of claim 15, wherein the outlet port of the injection syringe is connected to a catheter or needle which is then passed through the instrument channel of a medical endoscope and inserted into the body for the treatment of vesicoureteric reflux.

20. The method of claim 15, wherein the outlet port of the injection syringe is connected to a catheter or needle which is then passed through the instrument channel of a medical endoscope and inserted into the body for the treatment or urinary incontinence.

21. The method of claim 15, wherein the outlet port of the injection syringe is connected to a catheter or needle which is then inserted into the body for the treatment of emboli in the venous system.

22. An injection syringe for the injection of high viscosity paste or liquid, comprising a frame, a pair of handles mounted to said frame, at least one of which handles is a lever pivotally mounted to said frame incorporating a piston advancing means, an upper and lower cylinder chamber providing fluid connection therebetween, said upper chamber containing an inlet and outlet port, a one way ball-bearing inlet valve seated at the inlet port, a one way ball-bearing outlet valve seated at the outlet port, said lower cylinder chamber containing a piston having means connecting the piston to the piston advancing means on the lever pivot arm, wherein the inlet and outlet ports are sized relative to their respective ball-bearings to regulate the maximum internal delivery pressure in said upper cylinder chamber, wherein the piston advancing means comprises a semicircular cam track slidably engaging the piston connecting means for upwardly advancing said piston into said lower piston cylinder chamber as the piston connecting means slides along said cam track so that substantially all of the liquid or paste in the cylinders is forced through the one-way valve in the outlet cylinder chamber.

23. The injection syringe of claim 22 wherein the upper cylinder chamber projects beyond said frame.

24. The injection syringe of claim 22 which further includes an end space on the outlet side of the upper cylinder chamber to which an injection cannula can be mounted.

25. The injection syringe of claim 22 in which the inside diameter of the injection cannula at its end farthest from the end space on the outlet side of the upper cylinder chamber is smaller than the inside diameter of the cylinder.

26. The injection syringe of claim 25 in which the injection cannula is a needle.

27. The injection syringe of claim 25 in which the injection cannula is a catheter.

28. The injection syringe of claim 22 wherein a reservoir of high viscosity fluid or paste is attached by a connecting means to the inlet side of the upper cylinder chamber.

29. The injection syringe of claim 28 wherein the reservoir connecting means is a luer type connection.

30. The injection syringe of claim 22 wherein the length of the upper cylinder is a substantial multiple of its diameter.

31. The injection syringe of claim 22 in which the piston sealingly engaged the corresponding piston cylinder wall through an elastomeric O-ring seal.

32. The injection syringe of claim 22 wherein an extension spring is attached to the pivotally mounted handle so as to provide a retractive force to said handle.

33. The injection syringe of claim 22 wherein the syringe is manufactured from a plastic material.

34. The injection syringe of claim 22 wherein the syringe is manufactured from stainless steel.

35. The injection syringe of claim 22 wherein the one-way inlet and outlet ball-bearing valves are made from a fluoroelastomer material.

36. A method for introducing high viscosity medicaments into a patient comprising:
supplying the injection syringe of claim 16; and
charging the syringe by compressing and releasing the handle/lever combination wherein the pumping action provides a vacuum within the cylinders upon the downstroke of the piston and wherein the outlet ball-bearing valve seals and the inlet ball-bearing valve opens thereby charging the syringe; and advancing the medicament through the outlet check valve by a continued pumping action wherein the upstroke of he piston provides compression to the chambers and the inlet check valve seals and the outlet valve opens and the medicament is introduced into a body and restricted from moving back into the syringe.

37. The method of claim 36 wherein the high viscosity medicament is introduced into a medical endoscope.

38. The method of claim 36 wherein the high viscosity medicament is a suspension of polytetrafluoroethylene particles in glycerine and polysorbate.

39. The method of claim 36 wherein the high viscosity medicament is collagen.

40. The method of claim 36, wherein the outlet port of the injection syringe is connected to a catheter or needle which is then passed through the instrument channel of a medical endoscope and inserted into the body for the treatment of vesicoureteric reflux.

41. The method of claim 36, wherein the outlet port of the injection syringe is connected to a catheter or needle which is then passed through the instrument channel of a medical endoscope and inserted into the body for the treatment or urinary incontinence.

42. The methods of claim 36, wherein the outlet port of the injection syringe is connected to a catheter and then inserted into the body for the treatment of emboli in the venous system.

43. An injection syringe for injection of high viscosity pastes or fluids comprising:
a frame;
a pair of handles mounted to said frame, at least one of which is a lever pivotally mounted to said frame incorporating a piston advancing means, said handles further comprising a grip means which can be squeezed together to move the handles toward one another;
a first elongated upper cylinder chamber within said frame comprising:
a first end spaced from said frame having a one-way ball-bearing inlet valve whereby a feed of a high viscosity paste or fluid to be discharged can be drawn into said cylinder through said valve which restricts material from moving back into the source of said fluid or paste; and
a second end spaced from said frame to which an injection cannula can be mounted and having a one-way ball-bearing outlet valve to restrict material from moving back into the syringe; and
an opening to a second elongated lower cylinder piston chamber inter-connecting with said first cylinder chamber and extending into at least one of the handles mounted to said frame; and
a piston slidably fitted and sealingly engaging the second lower piston cylinder chamber and extending along the length of the lower cylinder chamber and having means converting the piston to the piston advancing means of said pivotally mounted handle, wherein the piston advancing means comprises a semi-circular cam track slidably engaging the piston connecting means for upwardly advancing said piston into said lower piston cylinder chamber as the piston connecting means slides along said cam track so that substantial all of the liquid placed in the cylinders is forced through the one-way valve and the outlet cylinder chamber.

44. An injection syringe for the injection of high viscosity paste or liquid into a human body, comprising:
a frame,
a pair of handles mounted to said frame, one of said handles being adapted to be grasped by the fingers of a user's hand and the other handle being adapted to be held in the palm of the user's hand, and wherein at least one of said handles is pivotally mounted to said frame and incorporates a piston advancing means,
an upper cylinder chamber containing an inlet port, an outlet port, a one way ball-bearing inlet valve seated at the inlet port, and a one way ball-bearing outlet valve seated at the outlet port,
a lower cylinder chamber containing a piston having means connecting the piston to the piston advancing means, wherein the upper and lower cylinder chambers provide fluid connection therebetween and wherein the piston advancing means comprises a semi-circular cam track slidably engaging the piston connecting means for upwardly advancing said piston into said lower piston cylinder chamber as the piston connecting means slides along said cam track so that substantially all of the liquid or paste in the cylinders is forced through the one-way valve in the outlet port of the upper cylinder and
a conduit including an initial portion coupled to the outlet port and extending to an end portion, wherein, when in an operative position, the end portion of the conduit is located within the human body for the deposition of high viscosity paste or liquid into a body passage.

45. A method for introducing high viscosity medicaments into a patient comprising:
supplying the syringe of claim 44, and
charging the syringe by compressing and releasing the handle/lever combination wherein the pumping action provides a vacuum within the cylinders upon the downstroke of the piston and wherein the outlet ball-bearing valve seals and opens, thereby charging the syringe; and
introducing the conduit into a human body such that the end portion of the conduit is located within a desired body passage; and
advancing the medicament through the outlet check valve by a continued pumping action wherein the upstroke of the piston seals and the outlet valve opens and the medicament is introduced into the human body through the end portion of the conduit and, wherein the medicament is restricted from moving back into the syringe.

* * * * *

UNITED STATES PATENT AND TRADEMARK OFFICE
CERTIFICATE OF CORRECTION

PATENT NO. :   5,304,147
DATED      :   April 19, 1994
INVENTOR(S):   Johnson et al It is certified that error appears in the above-identified patent and that said Letters Patent is hereby corrected as shown below:

Column 10, line 5, please delete "substantial" and insert --substantially--.

Signed and Sealed this

Twenty-sixth Day of July, 1994

Attest:

BRUCE LEHMAN

Attesting Officer

Commissioner of Patents and Trademarks